United States Patent
Hayes

(10) Patent No.: US 9,757,218 B2
(45) Date of Patent: Sep. 12, 2017

(54) LOOSE FLOSS METHOD OF INTER-DENTAL PLAQUE REMOVAL

(71) Applicant: Brian William Hayes, Fallsburg, NY (US)

(72) Inventor: Brian William Hayes, Fallsburg, NY (US)

(73) Assignee: Brian William Hayes, Fallsburg, NY (US)

( * ) Notice: Subject to any disclaimer, the term of this patent is extended or adjusted under 35 U.S.C. 154(b) by 0 days.

(21) Appl. No.: 15/530,022

(22) Filed: Nov. 22, 2016

(65) Prior Publication Data
US 2017/0105822 A1  Apr. 20, 2017

Related U.S. Application Data

(63) Continuation-in-part of application No. 14/793,650, filed on Jul. 7, 2015, now abandoned.

(51) Int. Cl.
*A61C 15/04* (2006.01)

(52) U.S. Cl.
CPC .................. *A61C 15/046* (2013.01)

(58) Field of Classification Search
CPC ....... A61C 15/02; A61C 15/04; A61C 15/043; A61C 15/045; A61C 15/046
USPC ......... 132/200, 321, 323–326, 328; 433/215, 433/216
See application file for complete search history.

(56) References Cited

U.S. PATENT DOCUMENTS

| | | | | |
|---|---|---|---|---|
| 1,990,404 A | * | 2/1935 | Doner | A61C 15/046 131/92 |
| 3,759,272 A | * | 9/1973 | Di Vincenti | A61C 15/046 132/326 |
| 3,886,956 A | * | 6/1975 | Cash | A61C 15/046 132/325 |
| 3,908,678 A | * | 9/1975 | Conn | A61C 15/046 132/325 |
| 4,022,229 A | * | 5/1977 | Minka | A61C 15/046 132/326 |
| 4,026,308 A | * | 5/1977 | Krivit | A61C 15/046 132/323 |
| 4,898,196 A | * | 2/1990 | Eason | A61C 15/046 132/324 |
| 5,269,331 A | * | 12/1993 | Tanriverdi | A61C 15/046 132/325 |

(Continued)

*Primary Examiner* — Tatiana Nobrega

(57) ABSTRACT

A comfortable way to daily remove inter-dental plaque would encourage dental hygiene and could improve health worldwide. The flossing by hand' method is the most effect but its adoption is limited by the dexterity of the user especially among young and old people. Many efforts have been made to make flossing easier by extending floss from a device held outside the mouth, but most designs use a fixed, stretched, length of floss at the tooth. The method of use for these devices is dictated by the physical form of the device needed to mount the fixed stretched length of floss. But the goal of flossing devices is to emulate the 'by hand' method. This invention starts with the 'by hand' method and designs this device 1 to perform it. The "Loose Floss Method of Inter-dental Plaque Removal' is strictly based on the 'by hand' method of flossing and provides a device 1 design exclusively to perform that method. closely without putting one's hands inside their mouth.

13 Claims, 4 Drawing Sheets

(56) References Cited

U.S. PATENT DOCUMENTS

| | | | | |
|---|---|---|---|---|
| 5,287,865 | A | * | 2/1994 | Fulton .................. A61C 15/046 |
| | | | | 132/323 |
| 5,657,780 | A | * | 8/1997 | Giacopuzzi .......... A61C 15/046 |
| | | | | 132/325 |
| 6,092,536 | A | * | 7/2000 | Owens ................. A61C 15/046 |
| | | | | 132/323 |
| 2011/0203609 | A1 | * | 8/2011 | Hardy .................. A61C 15/046 |
| | | | | 132/325 |

* cited by examiner

LOOSE FLOSS METHOD OF INTER-DENTAL PLAQUE REMOVAL

TECHNICAL FIELD

Dental hygiene inter-dental flossing method and in particular a inter-dental flossing method that necessarily employs a specifically designed floss delivery device.

BACKGROUND ART

Dental Hygiene Science has established that the accumulation of plaque containing bacteria in the sub gum "Gingival Sulcus" spaces of the mouth produces acids and enzymes that, if they accumulate, may lead to a hard mineral deposit called Calculus (Tartar) and may contribute to periodontal (gum) disease. It is established that if plaque is removed daily the teeth and gums remain healthy. Daily brushing of teeth is essential to controlling plaque. Daily that flossing between the teeth below the gum line within the gingival sulcus is an essential complement to daily tooth brushing above the gum line.

The common standard "Flossing by Hand" method (hereafter called the 'by hand' method) is, effectively, stated as follows:

A: Lightly wrap floss around the middle finger of both hands to secure the fixed ends of an approximately two inch span of floss.

B: Hold the floss with the thumb and index finger of each hand where it is wrapped around the corresponding middle fingers to be able to firmly hold the floss.

C: Place both hands into your mouth and draw the floss loosely over the tight space between the adjacent teeth to be flossed.

D: With your thumb and index fingers pressing the floss into the tight spot between adjacent teeth and gently draw the floss back and forth until the floss is straight through the tight spot between adjacent teeth, but still remaining above the gum line.

E: Relax the floss tension and draw the floss around the tooth by moving the fingers in along both sides of the line of teeth to create a wraparound "C" path of floss wrapping around the tooth.

F: Gently tension the floss and draw the floss back and forth, and up and down, around the surface of the tooth above and below the gum line simultaneously dislodging plaque and drawing the plaque out from the bottom of the gingival sulcus.

G: When finished with one tooth lift the floss loosely out of the gingival sulcus but staying below the tight spot between the adjacent teeth.

H: Draw the floss away in the opposite direction onto the adjacent tooth reversing the "C" shape of the floss along the tooth line and again wrapping the floss around the adjacent tooth and repeat step from step E:.

I: When finished flossing two adjacent teeth loosely lift the floss out of the gingival sulcus to below the tight spot between the adjacent teeth and preferably roll both hand's fingers over onto the same side (commonly the internal side) of the line of teeth and pull the floss out sideways employing the same processes as used in inserting floss in through a tight space between adjacent teeth. The sideways withdrawal forestalls damaging or lifting off dental caps or posts.

J: Advance fresh floss by unwinding and rewinding the floss around the middle fingers, and repeat throughout the mouth.

Many manual devices have been designed, with either brushes or floss, to deliver in-mouth inter-dental cleansing with devices that are held outside the mouth. These devices can be categorized as either "disposable" or "refillable".

Brushes are usually either disposable or have disposable bristles attached to a reusable handle; e.g. U.S. Pat. No. 4,828,420

Most disposable hand flossing devices are plastic yolks that have a fixed length of stretched floss across at the distal ends of a yolk at the; e.g. U.S. Pat. No. D577462 S.

Most refillable hand flossing devices also have a fixed length of floss stretched straight across a wide yolk at the distal ends, and employ a variety of ways to re-stretch a new fixed length of floss advanced from a floss source compartment in the handle; e.g. U.S. Pat. Nos. 3,759,272, 4,022,229, 5,287,865, 5269331. The default method for using fixed stretched flossing yolk devices is distinct from the common 'by hand' method (described above). The default fixed stretched floss yolk method of flossing is effectively as follows:

A: If the device is refillable you must insure that the floss is drawn across the yolk by two fixed, secured ends, otherwise a disposable device already has fixed tension span of floss. Then place the device in the mouth and place the floss onto the space between adjacent teeth B: Pull the floss tight back and forth across the tight spot by moving the yolk back and forth while lightly pressing the yolk in beyond the tight spot between the adjacent teeth.

C: Under the tight spot pull the stretched straight floss around the tooth as much as possible and draw the floss across the tooth by moving the yolk back and forth laterally.

D: When finished with one tooth lift the floss out of the gingival sulcus but remain below the tight spot between the adjacent teeth and draw the floss over toward the adjacent tooth and repeat (C:)

E: When finished with both adjacent teeth pull the floss across the tight spot by moving the floss back and forth by pulling the yolk back and forth while lightly pulling the yolk out above the tight spot between the adjacent teeth.

F: If the device is refillable, release the fixed ends, advance fresh floss, and re-secure the fixed ends. If the device is disposable, replace the device as needed. Repeat from A:.

Inter-dental brushes often have disposable conic shaped bristles radiating orthogonally from a central spine mounted on a handle. The method to use these brushes is simply press them in and out sideways through the space below the tight spot and above the gum line between adjacent teeth.

SUMMARY OF INVENTION

A method of flossing between adjacent teeth, by actively controlling floss movement using both hands to apply this method to a specifically designed device 1. Using this method with this device 1 can approximate the without putting one's hands inside their mouth. A sufficient description of this necessary device 1 suitable for applying this method is a hand held, inert, non-mechanical flossing "tuning fork style" yolk variant that is physically designed, and uniquely threaded, to facilitate a continuous, loose, flow of floss from an originating floss source area in its base through apertures in the yolk arms and freely exiting from the device 1 to be drawn away by the other hand. The device 1 may have a flat bottom so as to be stored in an upright position and should have a floss cutting notch in the base. This method using this device 1 can comfortably approximate the 'by hand' method. This method of fingertip pressure onto floss as it traverses this device 1 will tension, loosen, advance or withdraw the floss, while in use, as needed.

Technical Problem

The 'by hand" method is very effective but its use is limited by the dexterity of the user, especially among youths and seniors. The floss wrapped around an index finger often becomes too tight and produces the common "Blue Finger" of constricted blood circulation.

Inter-dental brushes cannot reach into the gingival sulcus.

Refillable devices with a fixed tight stretch of floss across a yolk, wide enough to pull the floss sideways, limits the flossing method to pulling the device back and forth sideways to draw the floss back and forth over the tooth. Devices with a fixed tight stretch of floss are relatively ineffective because they cannot approximate the wraparound "C" path of the 'by hand' flossing method. A fixed tight stretch of floss yolk also has no way to avoid "overshoot" when pressing floss into the tight spot between adjacent teeth thereby possibly damaging tie gum. The method of advancing floss in refillable devices is often very mechanically complex. If a fixed stretched length of floss gets immovably stuck between adjacent teeth or in braces the device gets stuck in the mouth also.

Disposable devices, either brushes or flossing devices are inefficient and, at present, environmentally unsound if not recycled.

Evidently; either the inability of most people to put both their hands in their mouth, or the inefficiency and waste of disposable devices, or the mechanical complexity of refillable designs have forestalled the wide adoption of daily flossing by most people. The problem is that everyone needs to easily remove plaque daily and a simple solution, readily adoptable by most of the human population, and addressing that need has heretofore not been achieved.

Solution to Problem

As FIGS. 1-4 will illustrate; this method is a solution that can comfortably remove inter-dental plaque build-up between adjacent teeth within the gingival sulcus of a tooth by actively using both hands to control a simple inert device 1 that, used according to this method, can approximate the flossing 'by hand' method closely, without putting one's hands inside their mouth. This method involves manual manipulation of floss passing through this device 1. The preferred device 1 would be a cast or injection molded single piece of plastic, formed as a (tuning fork type) monolithic yolk of two arms extending from a base containing a floss source. A circular recessed "Floss Source Area" (hereafter called the 'floss source' area 2 is formed in the base with a central spindle 3, to receive a free spinning spool of floss 4. A removable circular cap 5 can enclose the recessed area (the shape of the base may vary according to the floss supply source; herein we describe a floss "Spool" source only as an instance of a device 1 suited to this method). The first arm, arm 6, extends straight up from the base to its distal end. The second arm, arm 7, initially extends strait up from the other side of the base parallel to the first arm. The size of the arms is approximately 9 mm wide by 12 mm deep at the base and tapers to approximately 6 mm wide by 9 mm deep at the distal ends. The distance between the interior of the two arms at the base is approximately the width of an average human index finger, approximately 20 mm. Approximately halfway up the length of the first arm 6, the second arm 7 bends in, at an approximately fifty degree angle, straight toward the first arm 6. At a point where the distance between interior sides of both arms is approximately the width of an average human gum along the line of teeth (hereafter called the 'tooth line' 18), approximately 12 mm, the second arm 7 bends back at an opposite, but equal, angle and extends straight up, parallel to arm 6, to its distal end. The distal ends of the first arm 6 and the second arm 7 are equidistant from the base, at approximately 80 mm. An aperture 8 is formed from the recessed 'floss supply' area 2 through the base, opening onto the side of the base below the second arm 7. A second aperture 9 is formed on the second arm 7 near, but below, the bend in arm 7, from the outside of arm 7, toward arm 6. The surface of arm 7 between aperture 8 and aperture 9 must be flat because it is essential to the application of this method and is called the "Floss Advancement Control Surface" (called the 'advancement surface' 10). An aperture 11 is formed in arm 6, across from, and equidistant from the base, as aperture 9 on arm 7, and is aligned with aperture 9. An aperture 12 is formed at the distal end of the arm 6 from the outside of arm 6 toward arm 7. A final aperture 13 is formed at the distal end of arm 7, across from, and equidistant from the base as aperture 12 in arm 6, and is aligned with aperture 12.

The method used to thread the floss through this device 1 is essential to this method an is called the "Method 'S' Threading Path" (hereafter called the 'S path'). A user implements this method by first putting a spool of floss over the spindle 3 into the recessed area 2 and threads the floss 4 out through aperture 8 in the base of the device 1 and places a cover 5 (snap or screw on) over the recessed area 2 securing the spool placement. Then the floss is threaded into aperture 9 on arm 7. This outer, necessarily flat, surface between aperture 8 in the base and aperture 9 in arm 7 of the device 1 is essential to this method and is 'advancement surface' 10. The floss lies flat on the 'advancement surface'.

The floss is threaded out of aperture 9 on arm 7 across a span between the two arms into aperture 11 in arm 6. The span of floss between aperture 9 and aperture 11 is an essential element to this method and is called the "Floss Movement Control Span of Floss" (hereafter called the 'movement span' 14).

The floss is then threaded into aperture 12 at the distal end of arm 6, then out and across the span between the two arms, into aperture 13 at the distal end of arm 7, and leaves this device 1 out from aperture 13. The floss span between aperture 12 and aperture 13 is essential to this method and is called the "Working Span of Floss" (hereafter called the 'working span' 15). This threading creates an 'S path' for the floss that may be loosely, and continuously, be drawn from the 'floss source' area 2, through each aperture in the arms, and leaving this device 1 out through aperture 15 at the distal end of arm 7. The hand receiving and holding the used floss that exits this device 1 from aperture 15 is essential to this method and is called the "Exit Hand" (hereafter called the 'exit hand' 16). This particular threading on this particular device 1 is essential to implementing the current method of flossing between adjacent teeth in a manner that approximates the 'by hand' flossing method.

This method describes the 'advancement surface' 10 as the flat surface between aperture 8 at the base and aperture 9 on arm 7 where the middle finger pressure may stop the movement of fresh floss from the 'floss supply' area 2. The method describes the 'movement span' 14 as where the index finger rests and flexes down to either draw floss 4 back across the 'working span' 15, or advance the floss 4 from the 'floss source' area 2, depending on whether or not the floss advancement is stopped on the 'advancement surface' 10.

The 'working span' 15 is where the floss 4 is loosely wrapped around the tooth and then pulled along, parallel to the 'tooth line' to apply tension onto the surface of the tooth. The 'exit hand' 16 pulls used floss away, or brakes and balances the return tension on the floss 4 in the 'work span' 15 as needed.

Advantageous Effects of Invention

The principal advantage of this method is the simple adherence to the 'by hand' method of flossing. This method defines this preferred device 1 instead of the physical device determining the method. This method of hand and finger manipulation of loose floss mirrors the intuitive elements of 'by hand' flossing. This device 1 is not a active element of this method; it is a neutral inert support for the fingers to perform the method. Only the floss moves during flossing with this method, not this device 1. If the floss gets immovably stuck between adjacent teeth or in braces this method can loosen the floss and safely withdraw this device 1 out of the mouth and cut off the floss. This device 1 designed for this method would be an easy one piece injection mold manufacturing plan. This device 1 designed for this method could be dishwasher safe, and may last a lifetime.

DESCRIPTION OF EMBODIMENTS

Figure 1:
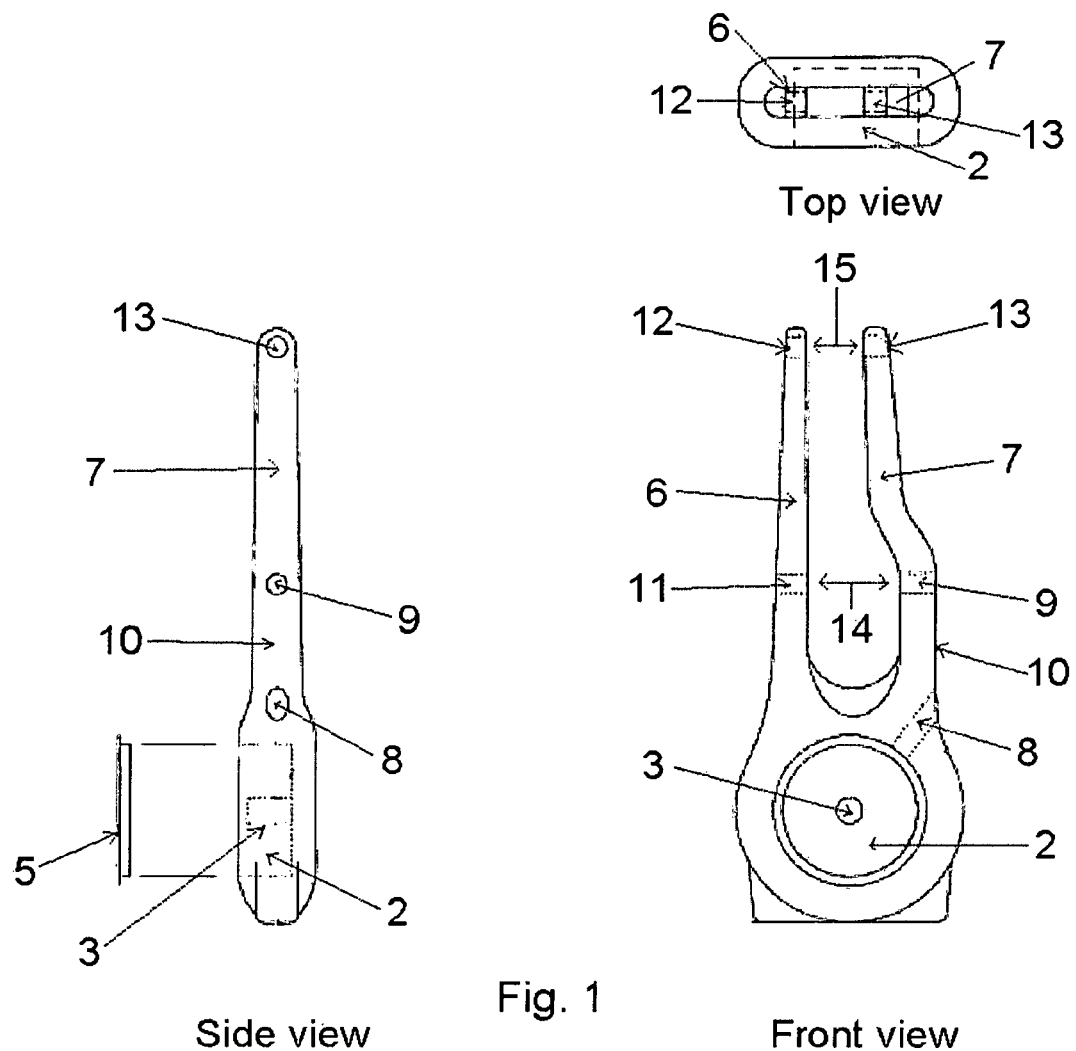
FIG. 1:
Orthogonal Project technical drawing of the front, side, and top view of a possible device 1 designed to be used by this method.
Figure 2:
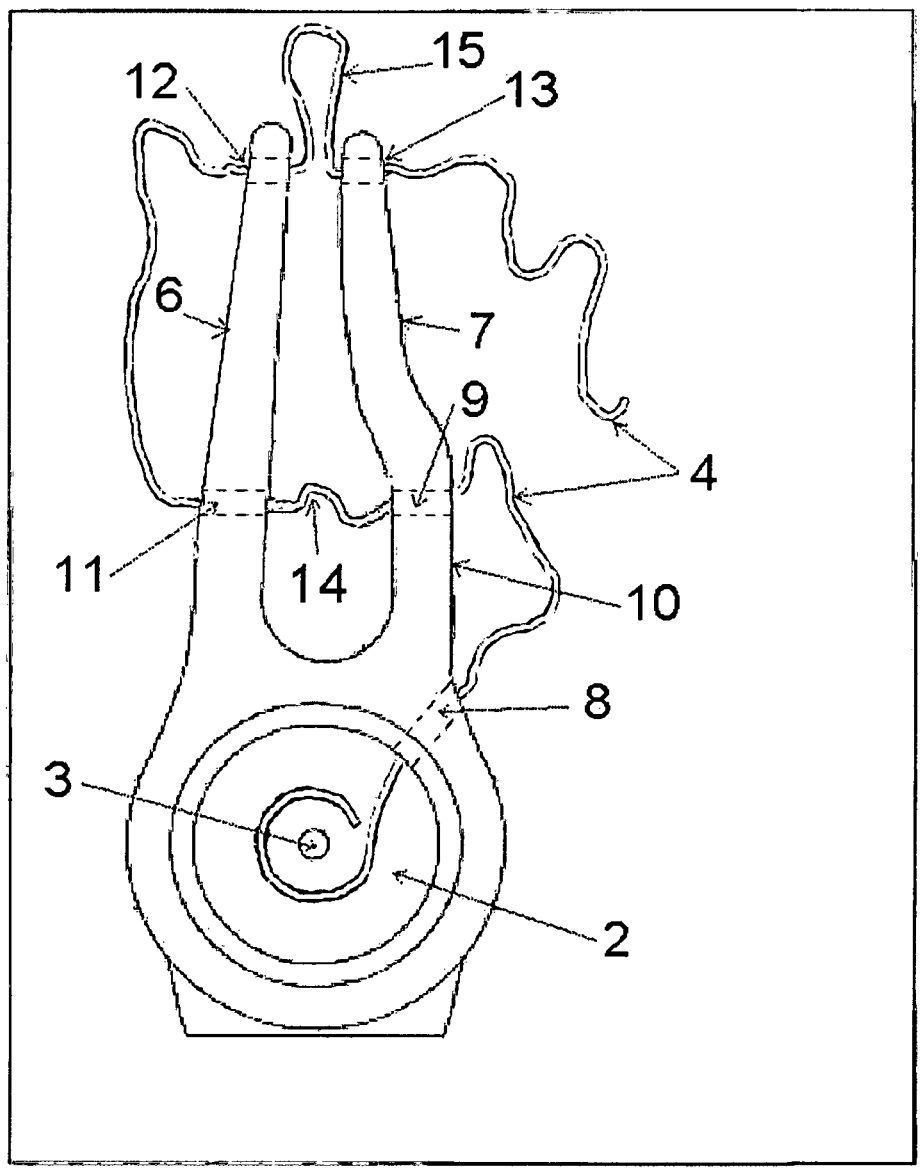
FIG. 2:
A view of this device 1 in FIG. 1 threaded but without the method applied to this device 1; illustrating the continuous, loose flow of floss in an "S" path through the apertures and out of the inert device 1.
Figure 3:
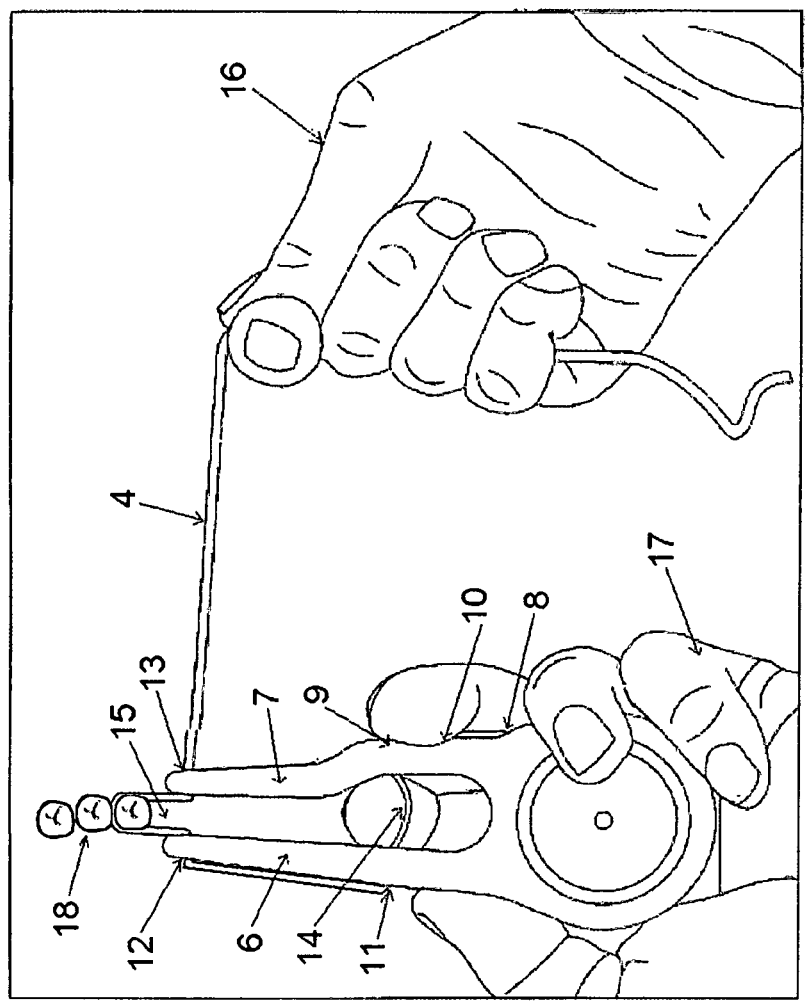
FIG. 3:
A view of this device 1 in FIG. 1 with the method applied in use. The drawing illustrates the use of the fingers and both hands. The 'control hand' 17 (defined below) holds this device 1 in the preferred grasp for the finger tip control of the floss 4 by this method. The other 'exit hand' 16 holds the exit floss with a balancing tension. The drawing also illustrates the wraparound "C" path of the floss 4 around a tooth.
Figure 4:
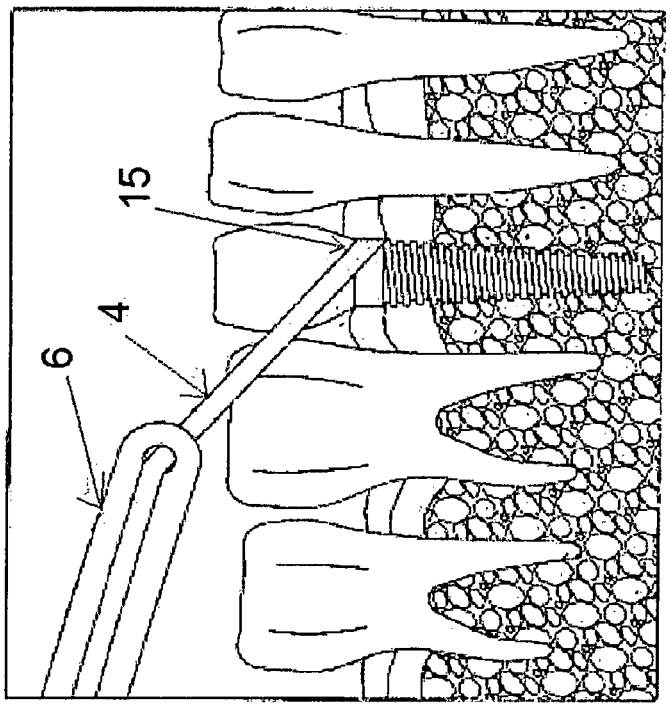
FIG. 4:
Two side views illustration of this method's wraparound path of the floss at the 'working span' 15 providing an approximation of the 'by hand' flossing method above and below the gum line (the exit floss has been omitted from the drawing for clarity).
Figure 4:
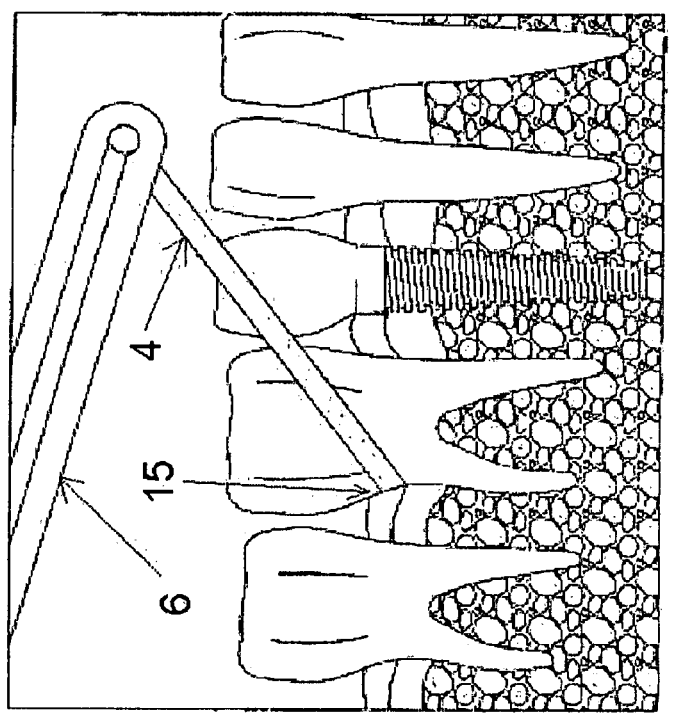

As illustrated in FIGS. 1-4, the present invention is a method using this device 1 design exclusively to apply the method. To apply this method using this device 1 first insert a spool of floss 4 into the recessed 'floss source' area 2 and thread this device 1 as defined above. The performance of this method requires a user to hold this device 1 in one hand and hold the exit floss in the other hand. The user then takes this device 1 into their "Controlling Hand of Choice" (hereafter called the 'control hand' 17) as one would hold a baseball. The thumb grasps the side of the base on the side of arm 6, the index finger raises up onto the 'movement span' 14 between arms 6 and 7, the middle finger rests on the 'advancement surface' 10, and two remaining fingers grasp the base of the below arm 7 at the side of the device 1. The index finger should fit into the lower, wider space between the arms and rest onto, and subsequently curve, the 'movement span' 14 of the floss 4. The thumb and opposing fingers establish a grip on the base in such a way to enable the index finger to flex down the 'movement span' 14, and for the middle finger to laterally apply, or release, stopping pressure on the 'advancement surface' 10.

The 'working span' 15 is placed into the mouth and loosely drawn over the tight spot between the adjacent teeth to be flossed, keeping the distal apertures 12 and 13 below the tight spot between adjacent teeth and above the gum line, and keeping the subsequent placement of the distal ends of arm 6 and arm 7 in place, unmoved. The middle finger pressure on the 'advancement surface' 14 stops the advancement of floss 4 from the 'floss source' area 2 and the 'exit hand' 16 stops the return of floss 4 across the 'working span' 15, so that by depressing the index finger onto the 'movement span' 14 the floss is drawn straight across the 'work span' 15 and below the tight spot between adjacent teeth safely above the gum line without moving the device 1 arms.

The user then releases finger pressure on the 'advancement surface' 10, flexes the 'movement span' 14 and pulls out floss 4 with the 'exit hand' 16 from aperture 13 at the distal end of arm 7 while simultaneously drawing the device 1 away along the 'tooth line' 18 to create a loose floss "C" pattern around the tooth allowing floss 4 to flow loosely and wrap around the tooth and into the gingival sulcus.

The user then applies pressure onto the 'advancement surface' 10 and stops the advancement of floss 4 from the 'floss source' area 2, and then presses down with the index finger flexing onto the 'movement span' 14 so that the 'exit hand' 16 must release floss back into the 'work span' 15 across the surface of the tooth. By repeatedly depressing and raising the index finger on the 'movement span' 14 and subsequently returning floss into or pulling floss out of the 'work span' 15 with a balanced tensile release and pull from the 'exit hand' 16, the floss 4 may be drawn back and forth through the 'work span' 15 and consequently back and forth around the curved surface of the tooth. Repeating this sequence buffs the floss 4 back and forth while the floss is wrapped around the tooth and into the gingival sulcus surface of the tooth and drawing out and dislodging plaque. When one tooth of an adjacent pair of teeth is cleaned the user loosely lifts the floss out of the "C" path back to a neutral loose, but, straight span of floss 4 across the 'working span' 15 while above the gum line but remaining below the tight spot between the adjacent teeth. Repeat the method on the adjacent tooth in the opposite direction.

According to need, advance fresh floss while the device 1 is still in-use by releasing pressure on the 'advancement surface' 10, stop the return of the floss 4 into the 'work span' 15 with the 'exit hand' 16 and flex the index finger on the 'movement span" 14 to pull in fresh floss 4 into the 'movement span' from the 'floss source' area 2, then by releasing the index finger off the 'movement span' 14 and pulling out floss 4 through aperture 13 on arm 7 with the 'exit hand" 16 fresh floss is passed into the 'work span" 15 in incremental lengths.

After each pair of adjacent teeth is flossed this method loosens the floss 4 and rolls both arms 6 and 7 over to the inside of the mouth wrapping the floss 4 over the tight spot between adjacent teeth sideways, then by reapplying the same method as entering into a tight spot, snap the floss out of the tight spot sideways, avoiding damage to caps and posts. The sideways roll over is made possible by the narrow width between the distal ends of arms 6 and 7 of the this method's device 1. Rinse the device 1 at the 'working span'

15 between each pair of adjacent teeth to remove plaque accumulation at aperture 12 and 13. Repeat the method throughout the mouth.

Citation List:
U.S. patent Documents:

| | | |
|---|---|---|
| 4,828,420 | May 9, 1989 | Masasuke Otsuka, Sumio Kuriyama, Hideyo Maniwa |
| D577,462 S | Sep. 23, 2008 | John M. Jansheski, Lex Shankle, Eric Mowell, Devon Moore, Eric E. Rios, Colin Farill |
| 3,759,272 | Sep. 18, 1973 | Angelo D. Di Vincenti |
| 4,022,229 | May 10, 1977 | Karlis Minka |
| 5,287,865 | Feb. 22, 1994 | Jesse O. Fulton |
| 5,269,331 | Dec. 4, 1993 | Verdi F. Tanriverdi |

The invention claimed is:

1. A method of flossing teeth comprising:
providing a dental flossing device comprising: a main body having a recessed area with a spindle therein and an aperture extending from a distal portion of the recessed area to an exterior of the main body, wherein first and second arms extend distally from the main body and the first and second arms are spaced from one another and each of the arms have connected ends secured to the main body and free distal ends; a first aperture formed in the first arm proximate the main body wherein a floss advancing surface extends between the aperture of the main body and the first aperture; a second aperture on the second arm proximate the main body and opposite the first aperture; a third aperture formed at the free distal end of the second arm and a fourth aperture formed at the free distal end of the first arm opposite the third aperture;
placing a spool of dental floss over the spindle into the recessed area;
threading the floss from the spool out through the aperture of the main body, along the floss advancing surface, through the first aperture, across the space between the first and second arms, through the second aperture, along a length of the second arm, through the third aperture, across the space between the free distal ends of the first and second arms and through the fourth aperture so that an exit span of floss extends outwardly from the fourth aperture;
with a first hand, grasping the dental flossing device by placing a first finger on a side of the second arm below the second aperture, placing a second finger on the floss between the first and second apertures and placing a third finger over the floss at the floss advancement surface;
with a second hand, grasping the exit span of floss;
then, inserting the floss disposed in the space between the first and second arms in an interproximal space between first and second teeth and repeatedly retracting and advancing the floss, such that the floss partially wraps around the first tooth;
wherein retracting of the floss is achieved by applying pressure to the floss at the advancement surface and applying pressure on the floss between the first and second apertures while the second hand permits the return of the exit span of floss into the space between the third and fourth apertures; and
wherein advancing of the floss is achieved by releasing pressure on the floss at the advancement surface and between the first and second apertures and, with the second hand, pulling the exit span of floss thereby moving the floss between the second and third aperture into the space between the third and fourth apertures.

2. The method of flossing teeth of claim 1, wherein while in the interproximal space, pulling or pushing the dental flossing device so that the floss partially wraps around the second tooth and repeatedly retracting and advancing the floss.

3. The method of flossing teeth of claim 1, removing the floss from the interproximal space.

4. The method of flossing teeth of claim 3, wherein after the removing step, performing the inserting step at another interproximal space.

5. The method of flossing teeth of claim 1, wherein the main body and the first and second arms are monolithic.

6. The method of flossing teeth of claim 1, wherein the method is performed without insertion of a user's hands in the mouth.

7. The method of flossing teeth of claim 1, wherein one of the first and second arms comprises a bent portion at a location between the main body and the free distal ends of the arm such that the space between the first and second arms is larger proximate the main body and smaller at the free distal ends.

8. A dental flossing device comprising:
a main body having a recessed area with a spindle therein and an aperture extending from a distal portion of the recessed area to an exterior of the main body, where the recessed area of the main body is capable of releasably securing a spool of dental floss;
a cap removably coupled to the main body, where the cap covers the recessed area of the main body;
first and second arms extending distally from the main body wherein the first and second arms are spaced from one another and each of the arms have proximal ends secured to the main body and free distal ends; a first aperture formed in a portion of the first arm proximate the main body; a second aperture formed in a portion of the second arm proximate the main body and opposite the first aperture; a third aperture formed at the free distal end of the second arm and a fourth aperture formed at the free distal end of the first arm opposite the third aperture;
the first arm having a bend in a portion thereof such that a distal space defined between interior surfaces of the first and second arms at the free distal ends thereof is smaller than a proximal space defined between interior surfaces of the first and second arms at the proximal ends, where the distal space is approximately 12 mm and the first and second arms are substantially parallel to one another in portions other than the bend;
the first and second arms each having a width, a thickness and a length defined between the proximal and distal ends, wherein the width and thickness are transverse to the length and taper toward the free distal end such that the width and the thickness at the proximal end are approximately 9 mm and 12 mm, respectively, and the width and the thickness at the free distal end are approximately 6 mm and 9 mm, respectively and the length is approximately 80 mm.

9. The dental flossing device of claim 8, wherein the main body and the first and second arms are monolithic.

10. The dental flossing device of claim 8, wherein the proximal space is approximately 20 mm.

11. The dental flossing device of claim 8, wherein the bend extends at an angle of approximately 50 degrees.

12. The dental flossing device of claim 8, wherein the bend is located approximately halfway up the length of the first arm.

13. The dental flossing device of claim 8, further comprising a spool of dental floss retained by the spindle in the recessed area of the main body.

\* \* \* \* \*